United States Patent [19]

Morozowich

[11] 4,154,926

[45] May 15, 1979

[54] INTER-PHENYLENE-PG-3,4-DIDEHYDROPIPERIDYLAMIDES

[75] Inventor: Walter Morozowich, Kalamazoo, Mich.

[73] Assignee: The Upjohn Company, Kalamazoo, Mich.

[21] Appl. No.: 898,226

[22] Filed: Apr. 20, 1978

Related U.S. Application Data

[63] Continuation-in-part of Ser. No. 788,455, Apr. 18, 1977, Pat. No. 4,100,192.

[51] Int. Cl.$^2$ .......................................... C07D 211/70
[52] U.S. Cl. ................................... 542/426; 542/429; 542/430; 546/262; 546/257; 546/258; 546/261

[58] Field of Search ........ 260/297 R, 294.8, 295 AM, 260/295 R, 293.76, 295 H; 542/429, 430, 426

[56] References Cited

U.S. PATENT DOCUMENTS

| | | | |
|---|---|---|---|
| 3,846,475 | 11/1974 | Crabbe et al. | 542/429 |
| 4,054,604 | 10/1977 | Bernady et al. | 260/557 R |

*Primary Examiner*—Arthur P. Demers
*Attorney, Agent, or Firm*—Robert A. Armitage

[57] ABSTRACT

The present invention relates to inter-phenylene-PG 3,4-didehydropiperidylamides. These compounds are pharmacological agents, being prolonged orally active platelet aggregation inhibitors in mammalian species. These compounds are accordingly useful for antithrombotic applications.

50 Claims, No Drawings

INTER-PHENYLENE-PG-3,4-DIDEHYDROPIPERIDYLAMIDES

CROSS REFERENCE TO RELATED APPLICATIONS

This application is a continuation-in-part of Ser. No. 788,455, filed Apr. 18, 1977, now issued as U.S. Pat. No. 4,100,192 on July 11, 1978.

The present invention relates to inter-phenylene-PG 3,4-didehydropiperidylamides, the essential material constituting a disclosure of which is incorporated here by reference from U.S. Pat. 4,110,192. In particular, the present invention relates to inter-phenylene-PG 3,4-didehydropiperidylamides of the unsubstituted inter-phenylene PG amides described in U.S. Pat. 4,110,192.

The present invention particularly relates to the following compounds:

3,7-inter-m-phenylene-3-oxa-4,5,6-trinor-11-deoxy-$PGF_{1\alpha}$, 3,4-didehydropiperidyl amide;

3,7-inter-m-phenylene-3-oxa-4,5,6-trinor-$PGF_{1\alpha}$, 3,4-didehydropiperdyl amide;

3,7-inter-m-phenylene-3-oxa-4,5,6-trinor-9-deoxy-$PGD_1$, 3,4-didehydropiperidyl amide;

3,7-inter-m-phenylene-3-oxa-4,5,6-trinor-$PGD_1$, 3,4-didehydropiperidyl amide;

3,7-inter-m-phenylene-3-oxa-4,5,6-trinor-9-deoxy-9,10-didehydro-$PGD_1$, 3,4-didehydropiperidyl amide;

3,7-inter-m-phenylene-3-oxa-4,5,6-trinor-$PGA_1$, 3,4-didehydropiperidyl amide;

3,7-inter-m-phenylene-3-oxa-4,5,6-trino-13,14-dihydro-11-deoxy-$PGE_1$, 3,4-didehydropiperidyl amide;

3,7-inter-m-phenylene-3-oxa-4,5,6-trinor-cis-13-$PGE_1$, 3,4-didehydropiperidyl amide;

3,7-inter-m-phenylene-3-oxa-4,5,6-trino-13,14-dihydro-$PGE_1$, 3,4-didehydropiperidyl amide;

3,7-inter-m-phenylene-3-oxa-4,5,6-trinor-$PGE_1$, 2,3-didehydropiperidyl amide;

15-epi-3,7-inter-m-phenylene-3-oxa-4,5,6-trinor-$PGE_1$, 3,4-didehydropiperidyl amide;

3,7-inter-m-phenylene-3-oxa-17-phenyl-4,5,6,18,19,20-hexanor-$PGE_1$, 3,4-didehydropiperidyl amide;

3,7-inter-m-phenylene-3-oxa-16-phenoxy-4,5,6,17,18,19,20-heptanor$PGE_1$, 3,4-didehydropiperidyl amide;

2a, 2b-dihomo-3,7-inter-m-phenylene-3-oxa-4,5,6-trinor-$PGE_1$, 3,4-didehydropiperidyl amide;

3,7-inter-m-phenylene-3-oxa-4,5,6-trinor-16,16-dimethyl-$PGE_1$, 3,4-didehydropiperidyl amide;

3,7-inter-m-phenylene-3-oxa-4,5,6-trinor-15-methyl-$PGE_1$, 3,4-didehydropiperidyl amide; and 3,7-inter-m-phenylene-3-oxa-4,5,6-trinor-$PGE_1$, 3,4-didehydropiperidyl amide.

I claim:

1. A prostaglandin analog of the formula

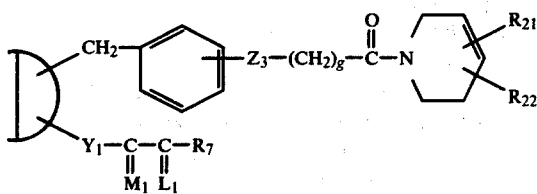

wherein D is

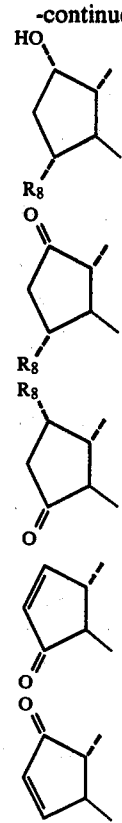

wherein $R_8$ is hydrogen or hydroxy;

wherein $Y_1$ is (1) trans—CH=CH—,
(2) cis—CH=CH—, or
(3) —$CH_2CH_2$—, wherein g is one, 2, or 3;

wherein $Z_3$ is oxa or methylene, with the proviso that $Z_3$ is oxa only when $R_3$ and $R_4$ are hydrogen or methyl, being the same or different;

wherein $L_1$ is

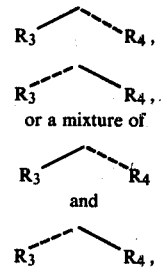

or a mixture of

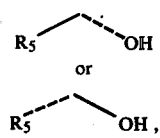

wherein $R_3$ and $R_4$ are hydrogen, methyl, or fluoro, being the same or different, with the provisio that one of $R_3$ and $R_4$ is methyl only when the other is hydrogen or methyl;

wherein $M_1$ is $$R_5 \diagup \diagdown OH$$

or $$R_5 \diagup \diagdown OH,$$

wherein $R_5$ is hydrogen or methyl;

wherein R₇ is (1) —(CH₂)$_m$—CH₃,

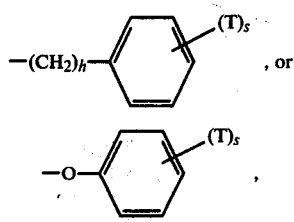

wherein h is zero to 3, inclusive, wherein m is one to 5, inclusive, s is zero, one, 2, or 3, T is chloro, fluoro, trifluoromethyl, alkyl of one to 3 carbon atoms, or alkoxy of one to 3 carbon atoms, the various T's being the same or different, with the provision that not more than two T's are other than alkyl; and wherein R₂₁ and R₂₂ are
  (i) hydrogen
  (ii) alkyl of one to 12 carbon atoms, inclusive;
  (iii) cycloalkyl of 3 to 10 carbon atoms, inclusive;
  (iv) aralkyl of 7 to 12 carbon atoms, inclusive;
  (v) phenyl;
  (vi) phenyl substituted with one, 2, or 3 chloro, alkyl of one to 3 carbon atoms, inclusive, hydroxy, carboxy, alkoxycarbonyl or one to 4 carbon atoms, inclusive, or nitro;
  (vii) carboxyalkyl of one to 4 carbon atoms, inclusive;
  (viii) carbamoylalkyl of one to 4 carbon atoms, inclusive;
  (ix) cyanoalkyl of one to 4 carbon atoms, inclusive;
  (x) acetylalkyl of one to 4 carbon atoms, inclusive;
  (xi) benzoylalkyl of one to 4 carbon atoms, inclusive;
  (xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
  (xiii) pyridyl;
  (xiv) pyridyl substituted by one, 2, or 3 chloro, alkyl of one to 3 carbon atoms, inclusive, or alkoxy of one to 3 carbon atoms, inclusive;
  (xv) pyridylalkyl of one to 4 carbon atoms, inclusive;
  (xvi) pyridylalkyl substituted by one, 2, or 3 chloro, alkyl of one to 3 carbon atoms, inclusive, hydroxy, alkoxy of one to 3 carbon atoms, inclusive;
  (xvii) hydroxyalkyl of one to 4 carbon atoms, inclusive;
  (xviii) dihydroxyalkyl of one to 4 carbon atoms; and
  (xix) trihydroxyalkyl of one to 4 carbon atoms;

with the further proviso that not more than one of R₂₁ and R₂₂ is other than hydrogen or alkyl.

2. A prostaglandin analog according to claim 1, wherein

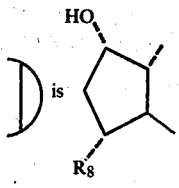

3. A prostaglandin analog according to claim 2, wherein R₈ is hydrogen.

4. 3,7-inter-m-Phenylene-3-oxa-4,5,6-trinor-11-deoxy-PGF $_{1α}$, 2,3-didehydropiperidylamide, a prostaglandin analog according to claim 3.

5. A prostaglandin analog according to claim 2, wherein R₈ is hydroxy.

6. 3,7-inter-m-Phenylene-3-oxa-4,5,6-trinor-PGF$_{1α}$, 3,4dihydropiperidyl amide a prostaglandin analog according to claim 5.

7. A prostaglandin analog according to claim 1, wherein

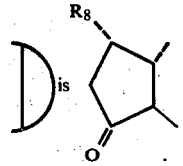

8. A prostaglandin analog according to claim 7, wherein R₈ is hydrogen.

9. 3,7-inter-m-Phenylene-3-oxa-4,5,6-trinor-9-deoxy-PGD₁, 3,4-dihydropiperidyl amide, a prostaglandin analog according to claim 8.

10. A prostaglandin analog according to claim 7, wherein R₈ is hydroxy.

11. 3,7-inter-m-Phenylene-3-oxa-4,5,6-trinor-PGD₁,3,4-dihydropiperidyl amide, a prostaglandin analog according to claim 10.

12. A prostaglandin analog according to claim 1, wherein

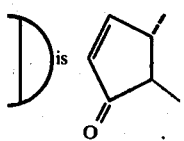

13. 3,7-inter-m-Phenylene-3-oxa-4,5,6-trinor-9-deoxy-9,10-didehydro-PGD₁, 3,4-dihydropiperidyl amide, a prostaglandin analog according to claim 12.

14. A prostaglandin analog according to claim 1, wherein

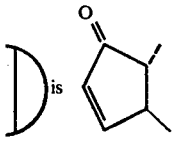

15. 3,7-inter-m-Phenylene-3-oxa-4,5,6-trinor-PGA₁,3,4-dihydropiperidyl amide, a prostaglandin analog according to claim 14.

16. A prostaglandin analog according to claim 1, wherein

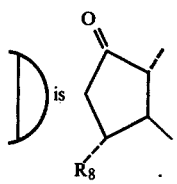 is

17. A prostaglandin analog according to claim 16, wherein $R_8$ is hydrogen.
18. 3,7-inter-m-Phenylene-3-oxa-4,5,6-trinor-13,14-dihyro11-deoxy-PGF$_1$,3,4-dihydropiperidyl amide, a prostaglandin analog according to claim 17.
19. A prostaglandin analog according to claim 16, wherein $R_8$ is hydroxy.
20. A prostaglandin analog according to claim 19, wherein $Y_1$ is cis-CH=CH-.
21. 3,7-inter-m-Phenylene-3-oxa-4,5,6-trinor-cis-13-PGE$_1$,3,4-dihydropiperidyl amide, a prostaglandin analog according to claim 20.
22. A prostaglandin analog according to claim 19, wherein $Y_1$ is $CH_2CH_2$—.
23. 3,7-inter-m-Phenylene-3-oxa-4,5,6-trinor-13,14-dihydroPGE$_1$, 3,4-dihydropiperidyl amide, a prostaglandin analog according to claim 22.
24. A prostaglandin analog according to claim 19, wherein $Y_1$ is trans—CH=CH—.
25. A prostaglandin analog according to claim 24, wherein $Z_3$ is methylene.
26. A prostaglandin analog according to claim 25, wherein $Z_3$ is attached to the phenyl ring in the position meta to methylene.
27. 3,7-inter-m-Phenylene-4,5,6,-trinor -PGE$_1$,3,4-dihydropiperidyl amide, a prostaglandin analog according to claim 26.
28. A prostaglandin analog according to claim 24, wherein $Z_3$ is oxa.
29. A prostaglandin analog according to claim 28, wherein $M_1$ is

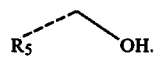

30. 15-epi-3,7-inter-m-Phenylene-3-oxa-4,5,6-trinor-PGE$_1$,3,4-dihydropiperidyl amide, a prostaglandin analog according to claim 29.
31. A prostaglandin analog according to claim 28, wherein $M_1$ is

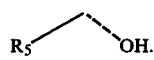

32. A prostaglandin analog according to claim 31, wherein $Z_3$ is attached to the phenyl ring in the position meta to methylene.

33. A prostaglandin analog according to claim 32, wherein $R_7$ is

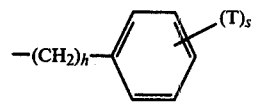

34. 3,7-inter-m-phenylene-3-oxa-17-phenyl-4,5,6,18,19,20 hexanor-PGE$_1$,3,4-dihydropiperidyl amide, a prostaglandin analog according to claim 33.
35. A prostaglandin analog according to claim 32, wherein $R_7$ is

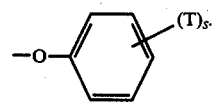

36. 3,7-inter-m-Phenylene-3-oxa-16-phenoxy-4,5,6,17,18,-19,20-heptanor-PGE$_1$,3,4-dihydropiperidyl amide, a prostaglandin analog according to claim 35.
37. A prostaglandin analog according to claim 32, wherein $R_7$ is —$(CH_2)_m$—$CH_3$.
38. A prostaglandin analog according to claim 37, wherein m is 3.
39. A prostaglandin analog according to claim 38, wherein g is 3.
40. 2a,2b-Dihomo-3,7-inter-m-phenylene-3-oxa-4,5,6-trinor-PGE$_1$,3,4-dihydropiperidyl amide, a prostaglandin analog according to claim 39.
41. A prostaglandin analog according to claim 38, wherein g is 1.
42. A prostaglandin analog according to claim 41, wherein at least one of $R_3$ and $R_4$ is methyl.
43. 3,7-inter-m-Phenylene-3-oxa-4,5,6-trinor-16,16-dimethyl-PGE$_1$,3,4-dihydropiperidyl amide, a prostaglandin analog according to claim 42.
44. A prostaglandin analog according to claim 41, wherein at least one of $R_3$ and $R_4$ is fluoro.
45. 3,7-inter-m-Phenylene-3-oxa-4,5,6-trinor-16,16-difluoro-PGE$_1$,3,4-dihydropiperidyl amide, a prostaglandin analog according to claim 44.
46. A prostaglandin analog according to claim 41, wherein $R_3$ and $R_4$ are both hydrogen.
47. A prostaglandin analog according to claim 46, wherein $R_5$ is methyl.
48. 3,7-inter-m-Phenylene-3-oxa-4,5,6-trinor-15-methyl-PGE$_1$ 3,4-dihydropiperidyl amide; a prostaglandin analog according to claim 47.
49. A prostaglandin analog according to claim 46, wherein $R_5$ is hydrogen.
50. 3,7-inter-m-Phenylene-3-oxa-4,5,6-trinor-PGE$_1$,3,4-dihydropiperidyl amide, a prostaglandin analog according to claim 49.

* * * * *

UNITED STATES PATENT OFFICE
CERTIFICATE OF CORRECTION

Patent No. 4,154,926      Dated May 15, 1979

Inventor(s) Walter Morozowich

It is certified that error appears in the above-identified patent and that said Letters Patent are hereby corrected as shown below:

Column 1, lines 32 and 36, "4,5,6-trino-" should read -- 4,5,6-trinor- --;

Column 4, line 13, "2,3-didehydropiperidylamide," should read -- 3,4-didehydropiperidyl amide, --;

Column 5, line 12-13, "dihyroll-" should read -- dihydro-11 --; line 22, "$Y_1$ is $CH_2CH_2$-" should read -- $Y_1$ is -$CH_2CH_2$- --.

UNITED STATES PATENT OFFICE
CERTIFICATE OF CORRECTION

Patent No. 4,154,926   Dated 15 May 1979

Inventor(s) W. Morozowich

It is certified that error appears in the above-identified patent and that said Letters Patent are hereby corrected as shown below:

Column 4, line 18, "3,4dihydropiperidyl amide" should read -- 3,4-didehydropiperidyl amide --; lines 34, 39, 53, and 65, "3,4-dihydropiperidyl amide" should read -- 3,4-didehydropiperidyl amide --;

Column 5, lines 11, 19, 24, 34-35, and 46, "3,4-dihydropiperidyl amide" should read -- 3,4-didehydropiperidyl amide --;

Column 6, lines 10-11, 21-22, 30, 37, 42, 49, and 54, "3,4-dihydropiperidyl amide" should read -- 3,4-didehydropiperidyl amide --.

*Signed and Sealed this*

*Twenty-fifth* Day of *September 1979*

[SEAL]

*Attest:*

*Attesting Officer*

LUTRELLE F. PARKER
*Acting Commissioner of Patents and Trademarks*